United States Patent

Kanda et al.

[11] Patent Number: 5,865,958
[45] Date of Patent: Feb. 2, 1999

[54] METHOD FOR SEPARATING CYCLOHEXENE

[75] Inventors: Yu Kanda; Toshio Uchibori, both of Kitakyushu; Takeshi Ishikawa; Akio Tsuboi, both of Kurashiki, all of Japan

[73] Assignee: Mitsubishi Chemical Corporation, Tokyo, Japan

[21] Appl. No.: 732,724

[22] Filed: Oct. 18, 1996

[30] Foreign Application Priority Data

Oct. 20, 1995 [JP] Japan ................................. 7-272436
Oct. 23, 1995 [JP] Japan ................................. 7-273967
Nov. 29, 1995 [JP] Japan ................................. 7-310823

[51] Int. Cl.$^6$ ................................ B01D 3/40; C07C 7/08
[52] U.S. Cl. ............................... 203/58; 203/74; 203/81; 585/808; 585/860; 585/865
[58] Field of Search ................................ 203/53, 58, 74, 203/73, 81; 585/860, 865, 808, 804, 807, 864

[56] References Cited

U.S. PATENT DOCUMENTS

| | | | |
|---|---|---|---|
| 2,840,511 | 6/1958 | Rylander et al. | 203/53 |
| 4,789,729 | 12/1988 | Nagira et al. | 528/496 |
| 4,955,468 | 9/1990 | Lee | 203/53 |
| 5,069,756 | 12/1991 | Berg | 203/51 |
| 5,085,740 | 2/1992 | Lee et al. | 203/58 |
| 5,334,774 | 8/1994 | Kogure et al. | 568/754 |
| 5,399,244 | 3/1995 | Gentry et al. | 203/53 |
| 5,405,505 | 4/1995 | Berg | 203/58 |
| 5,494,572 | 2/1996 | Horii et al. | 208/263 |

FOREIGN PATENT DOCUMENTS

| | | |
|---|---|---|
| 0360041 | 3/1990 | European Pat. Off. ........ 203/58 |
| 0 653 477 | 5/1995 | European Pat. Off. . |
| 52 5733 | 1/1977 | Japan . |
| 4 41441 | 2/1992 | Japan . |

OTHER PUBLICATIONS

Database WPI, Derwent Publications, AN 77–15211Y, JP 52 005 733, Jan. 17, 1977.

*Primary Examiner*—Virginia Manoharan
*Attorney, Agent, or Firm*—Oblon, Spivak, McClelland, Maier & Neustadt, P.C.

[57] ABSTRACT

Cyclohexene is separated from a mixture of cyclohexene and at least one of cyclohexane and benzene by subjecting the mixture to extractive distillation in the presence of an extraction solvent the formula:

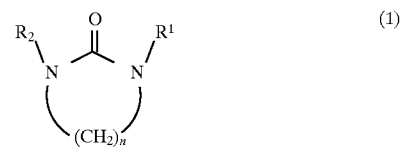

(1)

wherein $R^1$ and $R^2$ each is a $C_{1-10}$ alkyl group or hydrogen, and n is an integer of from 2–4, thereby preparing a fraction rich in cyclohexene.

7 Claims, 2 Drawing Sheets

CHE: Cyclohexene
CHX: Cyclohexane
BE : Benzene
NNDIN: Nitrogen-containing compound (1)

CHE: Cyclohexene
CHX: Cyclohexane
BE : Benzene
NNDIN: Nitrogen-containing compound (1)

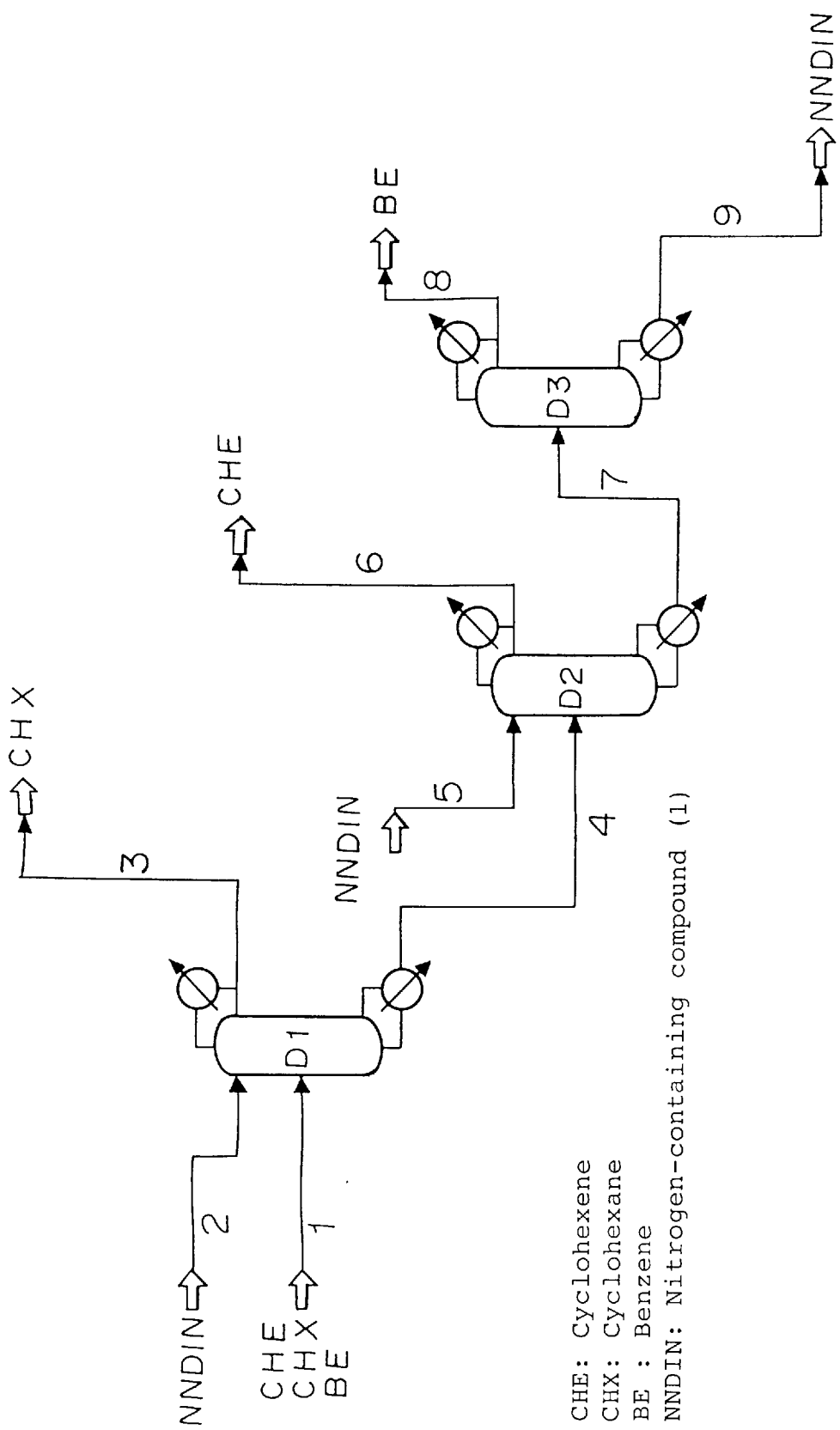

METHOD FOR SEPARATING CYCLOHEXENE

The present invention relates to a method for separating cyclohexene from a mixture comprising cyclohexene and at least one member selected from cyclohexane and benzene.

In recent years, an attention has been drawn to a method for producing cyclohexanol by hydrating cyclohexene obtainable by partial hydrogenation of benzene. The partial hydrogenation of benzene is carried out usually in the presence of a ruthenium catalyst and water, whereby a reaction mixture comprising cyclohexene, unreacted benzene and by-product cyclohexane, is usually obtained (e.g. Japanese Examined Patent Publications No. 5370/1991 and No. 19098/1990 and Japanese Unexamined Patent Publication No. 074141/1992).

In order to obtain cyclohexene of high purity from the reaction mixture of such partial hydrogenation of benzene, a method for separating cyclohexene from such a mixture becomes critical. However, boiling points of the three components i.e. cyclohexene, benzene and cyclohexane, are very close to one another, and it is difficult to separate them by usual distillation.

Accordingly, it is common to employ extractive distillation as a method for separating such a mixture. For such extractive distillation, methods have been proposed in which various extracting media, such as N,N-dimethylacetamide, adiponitrile, sulfolane, dimethyl malonate and dimethyl succinatey are used (e.g. Japanese Unexamined Patent Publications No. 1645724/1983, No. 1,645725/1983, No. 172323/1983, No. 295311/1987 and No. 41441/1992).

In such conventional extractive distillation employing various extracting media, the separation efficiency is not necessarily adequate, and when an expensive extraction solvent is used, such extractive distillation is economically disadvantageous. Further, as mentioned in the above-mentioned Japanese Unexamined Patent Publication No. 41441/1992, a decomposition product of an extraction solvent may sometimes brings about corrosion of the distillation apparatus or acts as a catalyst poison in various reactions, as an impurity in cyclohexene.

The present inventors have conducted extensive studies on a method for separating cyclohexene and as a result, have found it possible to solve all of the above-mentioned problems by extractive distillation employing a certain specific nitrogen-containing compound, or a mixed liquid of N-methyl-2-pyrrolidone and water, as an extraction solvent. The present invention has been accomplished on the basis of this discovery.

Thus, the present invention provides a method for separating cyclohexene from a mixture comprising cyclohexene and at least one member selected from cyclohexane and benzene, which comprises subjecting the mixture to extractive distillation to obtain a fraction rich in cyclohexene, wherein a nitrogen-containing compound of the following formula (1), or a mixed liquid of N-methyl-2-pyrrolidone and water, is used as an extraction solvent for the extractive distillation:

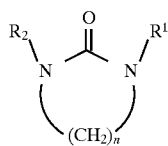
(1)

wherein each of $R^1$ and $R^2$ is a $C_{1-10}$ alkyl group or hydrogen, and n is an integer of from 2 to 4.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2 is a flow sheet illustrating another embodiment of the present invention which corresponds to the method ④ as described hereinafter.

Figure 1:
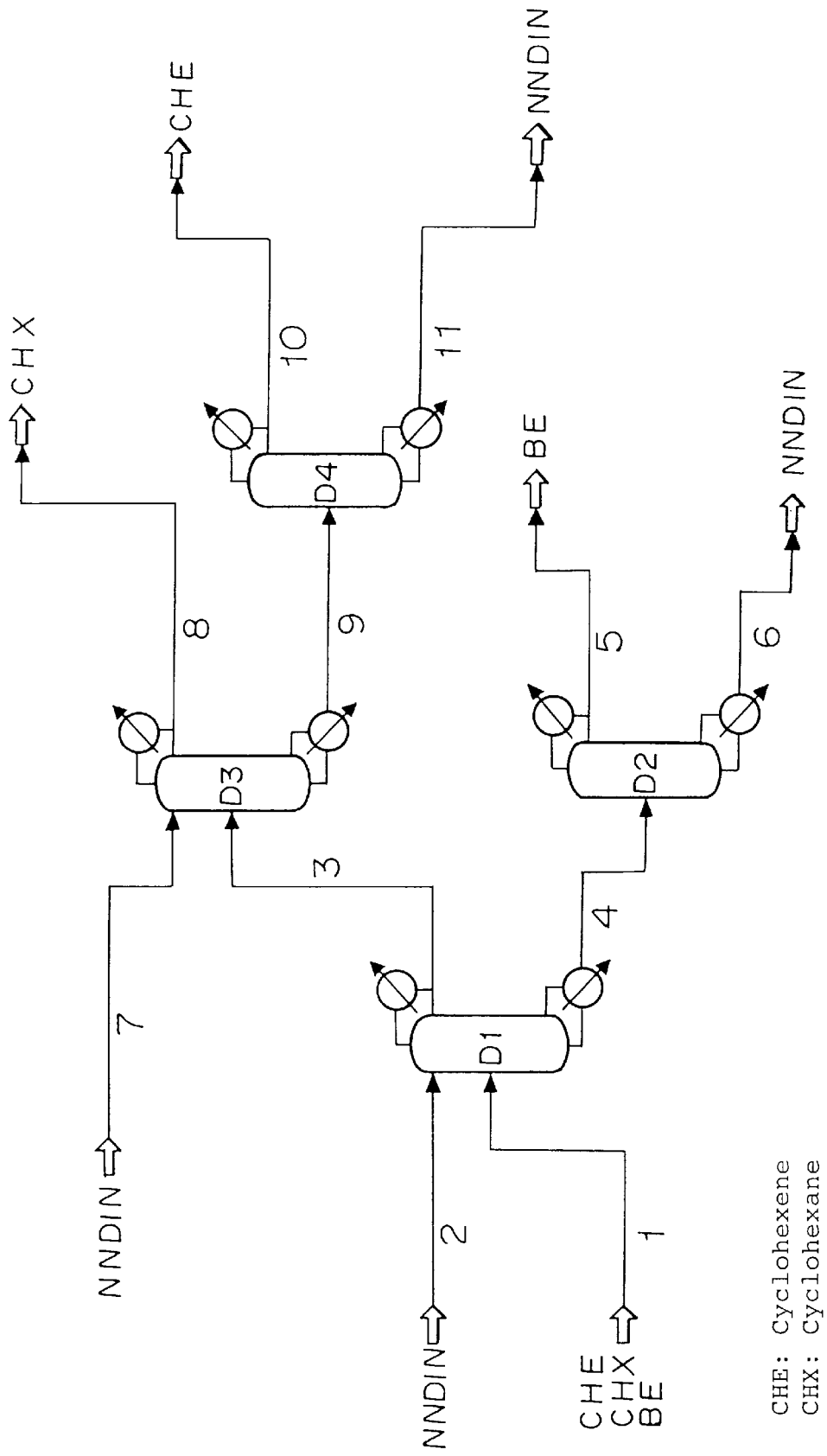
FIG. 1 is a flow sheet illustrating an embodiment of the present invention which corresponds to the method ③ as described hereinafter.

Now, the present invention will be described in detail with reference to the preferred embodiments.

In the present invention, the mixture which is subjected to extractive distillation is a mixture comprising cyclohexene and at least one member selected from the cyclohexane and benzene. A reaction mixture obtained by partial hydrogenation of benzene, may be mentioned as such a mixture to which the present invention is applicable.

The nitrogen-containing compound of the above formula (1) is preferably the one wherein each of $R^1$ and $R^2$ is a $C_{1-3}$ alkyl group, and n is 2. Specifically, such a compound may, for example, be 1,3-dimethyl-2-imidazolidinone or 1,3-diethyl-2-imidazolidinone, preferably 1,3-dimethyl-2-imidazolidinone. 1,3-Dimethyl-2-imidazolidinone is not only excellent as an extracting agent for separation useful in the present invention, but also relatively easily available for industrial purpose, thermally stable and free from corrosiveness, and it has a characteristic such that the toxicity is low. The nitrogen-containing compound of the formula (1) will hereinafter be referred to as "the nitrogen-containing compound (1)".

The following methods ① to ④ may be mentioned as typical embodiments for separating cyclohexene from a mixture containing cyclohexene by extractive distillation employing the nitrogen-containing compound (1) as an extraction solvent.

① A method wherein a mixture of cyclohexene and cyclohexane is subjected to extractive distillation by means of the nitrogen-containing compound (1) as the extraction solvent, so that cyclohexane is distilled from the top of the distillation column and a mixed liquid of cyclohexene and the nitrogen-containing compound (1), is withdrawn from the bottom of the column, and the mixed liquid is subjected to usual distillation to separate cyclohexene.

② A method wherein a mixture of cyclohexene and benzene is subjected to extractive distillation by means of the nitrogen-containing compound (1) as the extraction solvent, so that a mixed liquid of benzene and the nitrogen-containing compound (1), is withdrawn from the bottom of the distillation column, and cyclohexene is distilled from the top of the column to separate cyclohexene.

③ A method wherein a mixture of cyclohexene, cyclohexane and benzene, is subjected to first extractive distillation by means of the nitrogen-containing compound (1) as the extraction solvent, so that a mixed liquid of benzene and the nitrogen-containing compound (1), is withdrawn from the bottom of the distillation column, and a mixed liquid of cyclohexene and cyclohexane, is distilled from the top of the column, the distillate liquid is subjected to second extractive distillation by means of the nitrogen-containing compound (1) as the extraction solvent, so that cyclohexane is distilled from the top of the distillation column, and a mixed liquid of cyclohexene and the nitrogen-containing compound (1), is withdrawn from the bottom of the column, and the mixed liquid is subjected to distillation to separate cyclohexene.

④ A method wherein a mixture of cyclohexene, cyclohexane and benzene, is subjected to first extractive distillation by means of the nitrogen-containing compound (1) as the extraction solvent, so that cyclohexane is distilled from the top of the distillation column, and a mixed liquid of cyclohexene, benzene and the nitrogen-containing compound (1), is withdrawn from the bottom of the column, the mixed liquid is subjected to second extractive distillation, so that benzene and the nitrogen-containing compound (1) are withdrawn from the bottom of the distillation column, and cyclohexene is distilled from the top of the column to separate cyclohexene.

When extractive distillation is carried out in the above methods ① to ④, a distillation column is used which usually has a theoretical plate number of at least 10, preferably at least 20. The reflux ratio is usually from 0.5 to 30. If the reflux ratio is too small or too large, the separation efficiency deteriorates. If the reflux ratio is too large, the column system is obliged to be large. Usually, the nitrogen-containing compound (1) as the extraction solvent is supplied to an upper portion of the distillation column, and the mixture is supplied to a portion lower than the intermediate portion of the distillation column. At the upper portion, about 5 plates are usually provided as recovery plates. In each of the methods ① to ④, the extraction solvent is used usually in an amount of at least equivalent to the mixture, and the pressure at the top of the column is usually from 0.02 to 0.3 MPa. In the second extractive distillation in the method ④, the nitrogen-containing compound (1) as the extraction solvent is already contained in the mixed liquid supplied to the distillation step, but the nitrogen-containing compound (1) may be supplemented depending upon the composition or the amount of the components to be separated.

Now, more specific embodiments of the present invention will be described with reference to the drawings with respect to a method for separating and recovering cyclohexene from a mixture comprising three different compounds of cyclohexane, cyclohexene and benzene. In the drawings, the nitrogen-containing compound (1) is represented by "NNDIN" as an abbreviation.

FIG. 1 illustrates the above-mentioned method ③ which comprises firstly separating benzene from the mixture comprising cyclohexene, benzene and cyclohexane, and then separating cyclohexene and cyclohexane. Referring to FIG. 1, the mixture comprising three compounds of cyclohexane, cyclohexene and benzene, is supplied by a line 1 to a distillation column D1, and the nitrogen-containing compound (1) as an extraction solvent is supplied by a line 2 to the distillation column D1. In the distillation column D1, extractive distillation is carried out, whereby a mixture of cyclohexene and cyclohexane is withdrawn from the top of the column and transported by a line 3 to a distillation column D3, and from the bottom of the column, a mixture of benzene and the nitrogen-containing compound (1), is withdrawn and sent by a line 4 to a distillation column D2.

In the distillation column D2, benzene and the nitrogen-containing compound (1) are separated by distillation, whereby from the top of the column, benzene is withdrawn by a line 5, and from the bottom of the column, the nitrogen-containing compound (1) is withdrawn by a line 6.

On the other hand, to the distillation column D3, the mixture of cyclohexene and cyclohexane is supplied by the line 3, and the nitrogen-containing compound (1) is supplied by a line 7, to carry out extractive distillation. From the top of the column, cyclohexane is withdrawn by a line 8. From the bottom of the column, a mixture comprising cyclohexene and the nitrogen-containing compound (1), is withdrawn and sent to a distillation column D4 by a line 9.

In the distillation column D4, cyclohexene and the nitrogen-containing compound (1) are separated by distillation, whereby from the top of the column, cyclohexene is withdrawn by a line 10, and from the bottom of the column, the nitrogen-containing compound (1) is withdrawn by a line 11.

FIG. 2 illustrates the above method ④ which comprises firstly removing cyclohexane from the mixture comprising cyclohexene, benzene and cyclohexane and then separating cyclohexene and benzene. Referring to FIG. 2, the mixture comprising cyclohexene, benzene and cyclohexane, is sent by a line 1 to a distillation column D1, and the nitrogen-containing compound (1) is sent by a line 2 to the distillation column D1.

In the distillation column D1, extractive distillation is carried out, whereby from the top of the column, cyclohexane is withdrawn by a line 3, and from the bottom of the column, a mixture comprising benzene, cyclohexene and the nitrogen-containing compound (1), is withdrawn by a line 4, and the mixture is supplied to a distillation column D2. To the distillation column D2, the nitrogen-containing compound (1) is supplied also from a line 5.

Also in the distillation column D2, extractive distillation is carried out, whereby from the top of the column, cyclohexene is withdrawn by a line 6, and from the bottom of the column, a mixture of benzene and the nitrogen-containing compound (1), is withdrawn by a line 7 and supplied to a distillation column D3.

In the distillation column D3, benzene and the nitrogen-containing compound (1) are separated by distillation, whereby from the top of the column, benzene is withdrawn by a line 8, and from the bottom of the column, the nitrogen-containing compound (1) is withdrawn by a line 9.

Now, extractive distillation will be described in detail with respect to a case wherein a mixed liquid of N-methyl-2-pyrrolidone and water, is used as an extraction solvent for extractive distillation of a mixture containing cyclohexene. To carry out such extractive distillation, it is common to preliminarily prepare the mixed liquid of N-methyl-2-pyrrolidone and water and to supply the mixed liquid to the distillation column. However, N-methyl-2-pyrrolidone and water may separately be supplied to the distillation column. The amount of water in N-methyl-2-pyrrolidone is usually from 0.1 wt % to the soluble limit, preferably from 0.3 to 10 wt %, more preferably from 0.5 to 5 wt %. With the mixed liquid of N-methyl-2-pyrrolidone and water, not only separation of cyclohexene can be improved, but also the boiling point of the solvent can be lowered, whereby the heat load in distillation can be reduced.

The following methods ⑤ to ⑧ may be mentioned as typical embodiments for separating cyclohexene by extractive distillation of a mixture comprising cyclohexene and at least one member selected from cyclohexane and benzene by means of the mixed liquid of N-methyl-2-pyrrolidone and water, as the extraction solvent. The constructions of distillation columns for such methods ⑤ to ⑧, correspond to the constructions in the above methods ① to ④ wherein the nitrogen-containing compound (1) is used as the extraction solvent.

⑤ A mixture of cyclohexene and cyclohexane is subjected to extractive distillation in the presence of N-methyl- 2-pyrrolidone and water. From the top of the column, cyclohexane and water are distilled. The distillate is condensed and then subjected to oil-water separation, whereupon water is returned from the top of the column into the column for total reflux, and cyclohexane is preferably returned in a predetermined reflux ratio, while the rest of cyclohexane is withdrawn. In this case, from the bottom of the column, water is withdrawn together with cyclohexene and N-methyl-2-pyrrolidone, and from the withdrawn liquid, cyclohexene is separated. Specifically, the withdrawn liquid is subjected to distillation, whereby from the top of the column, cyclohexene and water are distilled, and the distillate is condensed and then subjected to oil-water separation, whereupon water may be returned in its entire amount from the top of the column into the column, and cyclohexene is preferably returned in a predetermined reflux ratio, while the rest of cyclohexene is withdrawn for recovery. From the bottom of the column, N-methyl-2-pyrrolidone and water are withdrawn. Water separated by the second oil-water separation may not be returned into the column, and in that case, N-methyl-2-pyrrolidone is withdrawn from the bottom of the column. Water obtained by oil-water separation may be reused as an extraction solvent.

⑥ A mixture of cyclohexene and benzene, is subjected to extractive distillation in the presence of N-methyl-2-pyrrolidone and water. From the top of the column, cyclohexene and water are distilled. The distillate is condensed and then subjected to oil-water separation, whereupon water is returned from the top into the column for total reflux, and cyclohexene is preferably returned in a predetermined reflux ratio, while the rest of cyclohexene is withdrawn for recovery. In this case, from the bottom of the column, water is withdrawn together with benzene and N-methyl-2-pyrrolidone. Water obtained by oil-water separation, may be reused as an extraction solvent.

⑦ A mixture of cyclohexene, cyclohexane and benzene is subjected to first extractive distillation in the presence of N-methyl-2-pyrrolidone and water. From the top of the column, cyclohexene, cyclohexane and water are distilled. The distillate is condensed and then subjected to oil-water separation, whereupon water is returned from the top into the column for total reflux, and each of cyclohexene and cyclohexane is preferably returned in a predetermined reflux ratio, while the rest is withdrawn. In this case, from the bottom of the column, water is withdrawn together with benzene and N-methyl-2-pyrrolidone. Cyclohexane and cyclohexene withdrawn from the top of the column, is subjected to second extractive distillation in the presence of N-methyl-2-pyrrolidone and water, whereby from the top of the column, cyclohexane and water are distilled, and the distillate is condensed and then subjected to oil-water separation, whereupon water is returned in its entire amount from the top into the column, and cyclohexane is preferably returned in a predetermined reflux ratio, while the rest of cyclohexane is withdrawn. In this case, from the bottom of the column, water is withdrawn together with cyclohexene and N-methyl-2-pyrrolidone. The withdrawn liquid is usually subjected to distillation, whereby from the top of the column, cyclohexene and water are distilled, and the distillate is condensed and then subjected to oil-water separation, whereupon water may be returned in its entire amount from the top into the column, and cyclohexene is preferably returned in a predetermined reflux ratio, while the rest of cyclohexene is withdrawn for recovery. From the bottom of the column, N-methyl-2-pyrrolidone and water are withdrawn. Water separated by the second oil-water separation may not be returned into the column, and in that case, N-methyl-2-pyrrolidone is withdrawn from the bottom of the column. Water obtained by oil-water separation, may be reused as an extraction solvent.

⑧ A mixture of cyclohexene, cyclohexane and benzene, is subjected to first extractive distillation in the presence of N-methyl-2-pyrrolidone and water. From the top of the column, cyclohexane and water are distilled. The distillate is condensed and then subjected to oil-water separation, whereupon water is returned from the top into the column for total reflux, and cyclohexane is preferably returned in a predetermined reflux ratio, while the rest of cyclohexane is withdrawn. In this case, from the bottom of the column, water is withdrawn together with cyclohexene, benzene and N-methyl-2-pyrrolidone. This withdrawn liquid is subjected to second extractive distillation, whereby from the top of the column, cyclohexene and water are distilled, and the distillate is condensed and then subjected to oil-water separation, whereupon water is returned in its entire amount from the top into the column, and cyclohexene is preferably returned in a predetermined reflux ratio, while the rest of cyclohexene is withdrawn for recovery. In this case, from the bottom of the column, water is withdrawn together with benzene and N-methyl-2-pyrrolidone.

In the extractive distillation, water forms an azeotrope together with the column top component, and thus it is distilled and can be withdrawn. However, in order to make it unnecessary to supplement fresh water to N-methyl-2-pyrrolidone withdrawn from the bottom of the column, or in order not to let water be contained in the column top component, it is preferred that, as in the above methods ⑤ to ⑧, water and the column top component distilled from the top of the column, are condensed, and the condensed liquid is subjected to oil-water separation, whereupon water is returned in its entire amount for total reflux for extractive distillation, whereby water is withdrawn from the bottom of the column together with N-methyl-2-pyrrolidone, etc. Further, water obtained by oil-water separation, may be reused as an extraction solvent.

When extractive distillation is carried out by the above methods ⑤ to ⑧, it is common to employ a distillation column having a theoretical plate number of at least 15, preferably at lest 20. Usually, the mixed solvent of N-methyl-2-pyrrolidone and water, as the extraction solvent, is supplied to an upper portion of the distillation column, and the mixture is supplied to a portion lower than the intermediate portion of the distillation column. In each of the methods ⑤ to ⑧, the extraction solvent is used usually in an amount of at least equivalent to the mixture, and the pressure at the top of the column is usually from 0.02 to 0.3 MPa. The reflux ratio is not particularly limited, but, for example, in the case of a mixture of cyclohexane and cyclohexene, the reflux ratio is usually from 2 to 10, preferably from 3 to 6. In the second extractive distillation in the method ⑧, the mixed solvent of N-methyl-2-pyrrolidone and water, as the extraction solvent, is already contained in the mixed liquid supplied to the distillation step, but a mixed solvent of N-methyl-2-pyrrolidone and water, may be supplemented for distillation depending upon the composition or the amount of the components to be separated.

In each method for obtaining cyclohexene, it is possible that water is distilled from the top of the column, but in order to make it unnecessary to add water afresh and to avoid a loss of a component soluble in water, it is preferred that water distilled from the top of the column is returned in its entire amount after it is separated from other components by oil-water separation, and water is withdrawn from the bottom of the column together with N-methyl-2-pyrrolidone.

Now, the present invention will be described in further detail with reference to Examples. However, it should be understood that the present invention is by no means restricted to such specific Examples. In the following Examples, "parts" and "%" means "parts by weight" and "% by weight" unless otherwise specified.

EXAMPLE 1

Extractive distillation was carried out at a reflux ratio of 20 under a column top pressure of 0.1 MPa, while introducing 25 parts/hr of cyclohexane, 45 parts/hr of cyclohexene and 38 parts/hr of benzene to a position at 1360 mm from the top of a packing type distillation column of a 25 φ SULZER LABO PACKING packed column having a packing height of 2.8 m (HETP=65 mm, distillation column theoretical plate number=43 plates) and introducing 320 parts/hr of 1,3-dimethyl-2-imidazolidinone to a position at 330 mm from the top of the column. As a result, from the top of the column, cyclohexane having a purity of 98.6% was obtained at a rate of 23 parts/hr, and from the bottom of the column, 405 parts of a mixture comprising cyclohexene, benzene and 1,3-dimethyl-2-imidazolidinone, was obtained.

COMPARATIVE EXAMPLE 1

Extractive distillation was carried out in the same manner as in Example 1 except that as the extraction solvent, N,N-dimethylacetamide was used instead of 1,3-dimethyl-2-imidazolidinone. As a result, from the top of the column, cyclohexane having a purity of 95.5% was obtained at a rate of 23 parts/hr.

EXAMPLE 2

Using the same distillation column as used in Example 1, extractive distillation was carried out at a reflux ratio of 5 under a column top pressure of 0.1 MPa, while introducing a mixture comprising cyclohexene and benzene obtained in the same manner as in Example 1 to a position at 2100 mm from the top of the column at a rate of 52.8 parts/hr of cyclohexene and 32.4 parts/hr of benzene and introducing 320 parts/hr of 1,3-dimethyl-2-imidazolidinone to a position at 330 mm from the top of the column. As a result, from the top of the column, cyclohexene having a purity of 98.2% was obtained at rate of 48.7 parts/hr, and from the bottom of the column, a very small amount of cyclohexene and 367 parts of a mixture of benzene and 1,3-dimethyl-2-imidazolidinone, were obtained.

EXAMPLE 3

Using the same packing type distillation column as used in Example 1, extractive distillation was carried out at a reflux ratio of 10 under a column top pressure of 0.1 MPa, while introducing a mixture comprising cyclohexene and benzene obtained in the same manner as in Example 1 to a position at 2100 mm from the top of the column at a rate of 52.8 parts/hr of cyclohexene and 32.4 parts/hr of benzene and introducing 320 parts/hr of 1,3-dimethyl-2-imidazolidinone to a position at 330 mm from the top of the column. As a result, from the top of the column, cyclohexene having a purity of 93.2% was obtained at a rate of 51.1 parts/hr, and from the bottom of the column, 354 parts/hr of a mixture of benzene and 1,3-dimethyl-2-imidazolidinone, was obtained.

EXAMPLE 4

Using the same distillation column as used in Example 1, extractive distillation was carried out at a reflux ratio of 5 under a column top pressure of 0.1 MPa, while introducing a mixture comprising cyclohexene and benzene obtained in the same manner as in Example 1 to a position at 2100 mm from the top of the column at a rate of 52.3 parts/hr of cyclohexene and 32.4 parts/hr of benzene and introducing 320 parts/hr of 1,3-dimethyl-2-imidazolidinone to a position at 330 mm from the top of the column. As a result, from the top of the column, cyclohexene having a purity of 98.2% was obtained at a rate of 49.0 parts/hr, and from the bottom of the column, a very small amount of cyclohexene and 356 parts of a mixture of benzene and 1,3-dimethyl-2-imidazolidinone, were obtained.

EXAMPLE 5

Using the same distillation column as used in Example 1, extractive distillation was carried out at a reflux ratio of 5 under a column top pressure of 0.1 MPa, while introducing a mixture comprising cyclohexene and benzene obtained in the same manner as in Example 1, to a position at 2100 mm from the top of the column at a rate of 52.1 parts/hr of cyclohexene and 37.7 parts/hr of benzene and introducing 423 parts/hr of 1,3-dimethyl-2-imidazolidinone to a position at 330 mm from the top of the column. As a result, from the top of the column, cyclohexene having a purity of 99.7% was obtained at a rate of 48.7 parts/hr, and from the bottom of the column, a very small amount of cyclohexene and 464 parts of a mixture comprising benzene and 1,3-dimethyl-2-imidazolidinone, were obtained.

EXAMPLE 6

Distillation simulation was carried out using static simulator soft ASPEN, manufactured by ASPENTEC Co. (the physical property model for the simulation was the one calculated as a homogeneous system by correction UNIFAC, and the same applies to the results of distillation simulation given hereinafter). As a result, extractive distillation is carried out at a reflux ratio of 8 under a column top pressure of 0.1 MPa, while introducing 750 parts/hr of cyclohexane and 3000 parts/hr of cyclohexene and 2500 parts/hr of benzene to the 12th plate from the top of the distillation column having a theoretical plate number of 22 plates (each of a condenser at the top and a reboiler at the bottom is counted as one plate) and introducing 3000 parts/hr of 1,3-dimethyl-2-imidazolidinone to the 4th plate from the top of the column. As a result, from the top of the column, a mixture of cyclohexane and cyclohexene (19.96% of cyclohexane and 77.45% of cyclohexene) containing 2.58% of benzene, is obtained.

EXAMPLE 7

Distillation simulation was carried out using static simulator soft ASPEN, manufactured by ASPENTEC Co. As a result, extractive distillation is carried out at a reflux ratio of 20 under a column top pressure of 0.1 MPa, while introducing 750 parts/hr of cyclohexane and 3000 parts/hr of cyclohexene to the 50th plate from the top of a distillation column having a theoretical plate number of 62 plates (each of a condenser at the top and a reboiler at the bottom is counted as one plate) and introducing 20000 parts/hr of 1,3-dimethyl-2-imidazolidinone to the 5th plate from the top of the column. As a result, from the top of the column, cyclohexane containing 30.0% of cyclohexene is obtained, and from the bottom of the column, a mixture of cyclohexene and 1,3-dimethyl-2-imidazolidinone (12.9% of cyclohexene and 87.0% of 1,3-dimethyl-2-imidazolidinone) containing 0.1% of cyclohexane, is obtained.

EXAMPLES 8 to 13

Distillation simulation was carried out using static simulator soft ASPEN, manufactured by ASPENTEC Co. (the physical property model for the simulation was the one calculated as 3 phase distillation). Extractive distillation is carried out at a reflux ratio as identified in Table 1 under a column top pressure of 0.1 MPa, while introducing 3000 parts/hr of cyclohexane and 3000 parts/hr of cyclohexene to the 14th plate from the top of a distillation column having a theoretical plate number of 18 plates, at 80° C. under 1 atm and introducing 30000 parts/hr (of which 500 parts are water) of a solvent mixture of N-methyl-2-pyrrolidone and water to the 4th plate from the top of the column, at 80° C. under 1 atm. Here, cyclohexane and water distilled from the top of the column are subjected to oil-water separation, whereupon water is returned in its entire amount to the 4th plate from the top of the column. As a result, from the top of the column, cyclohexane having a purity as identified in Table 1 is obtained at a rate of 3000 parts/hr, and from the bottom of the column, a mixture comprising cyclohexene, N-methyl-2-pyrrolidone and water, is obtained.

Cyclohexene can readily be separated from N-methyl-2-pyrrolidone and water. This means that higher the purity of cyclohexane, the higher the purity of cyclohexene obtainable.

COMPARATIVE EXAMPLES 2 to 6

Distillation simulation was carried out using static simulator soft ASPEN, manufactured by ASPENTEC Co. (the physical property model for the simulation was the one calculated as a homogeneous system by correction UNIFAC). Extractive distillation is carried out in the same manner as in Example 8 except that as the extraction solvent, N-methyl-2-pyrrolidone was used alone (3000 parts/hr) instead of the mixed liquid of N-methyl-2-pyrrolidone and water, and cyclohexane was taken out alone from the top of the column. The results are shown in Table 1.

TABLE 1

|  | Reflux ratio | Purity of cyclohexane (%) |
|---|---|---|
| Example 8 | 2 | 87.7 |
| Example 9 | 3 | 90.5 |
| Example 10 | 4 | 90.6 |
| Example 11 | 5 | 89.2 |
| Example 12 | 6 | 87.8 |
| Example 13 | 7 | 86.6 |
| Comparative Example 2 | 2 | 80.4 |
| Comparative Example 3 | 4 | 84.1 |
| Comparative Example 4 | 6 | 85.5 |
| Comparative Example 5 | 8 | 85.8 |
| Comparative Example 6 | 10 | 85.7 |

EXAMPLES 14 to 22

Extractive distillation is carried out in the same manner as in Example 8 except that the reflux ratio is changed to 3, and the flow rate of water in the mixed solvent is changed to the rate as identified in Table 2. The results are shown in Table 2.

TABLE 2

|  | Flow rate of water (parts/hr) | Purity of cyclohexane (%) |
|---|---|---|
| Example 14 | 200 | 89.3 |
| Example 15 | 400 | 90.2 |
| Example 16 | 500 | 90.5 |
| Example 17 | 600 | 90.6 |
| Example 18 | 800 | 90.4 |
| Example 19 | 1000 | 89.9 |
| Example 20 | 1200 | 89.3 |
| Example 21 | 1400 | 88.3 |
| Example 22 | 1600 | 86.5 |

According to the present invention, cyclohexene of high purity can be obtained efficiently from a mixture comprising cyclohexene and at least one member selected from cyclohexane and benzene. The specific nitrogen-containing compound or the mixed system of N-methyl-2-pyrrolidone and water, used as an extraction solvent in extractive distillation of the present invention, is chemically stable and relatively inexpensive. Accordingly, the present invention is expected to be a very advantageous method for producing cyclohexene of high purity on an industrial scale over a long period of time.

What is claimed is:

1. A method for separating cyclohexene from a mixture comprising cyclohexene and at least one member selected from a group consisting of cyclohexane and benzene, which comprises subjecting the mixture to extractive distillation to obtain a fraction rich in cyclohexene, wherein a nitrogen-containing compound of the following formula (1), or a is used as an extraction solvent for the extractive distillation:

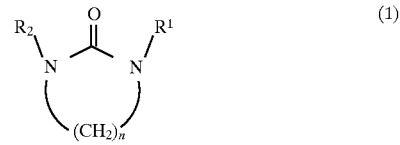

wherein each of $R^1$ and $R^2$ is a $C_{1-10}$ alkyl group or hydrogen, and n is an integer of from 2 to 4.

2. The method for separating cyclohexene according to claim 1, wherein in the formula (1), each of $R^1$ and $R^2$ is a $C_{1-3}$ alkyl group, and n is 2.

3. The method for separating cyclohexene according to claim 1, wherein the nitrogen-containing compound of the formula (1) is 1,3-dimethyl-2-imidazolidinone.

4. The method for separating cyclohexene according to claim 1, wherein a mixture of cyclohexene and cyclohexane is subjected to extractive distillation by means of the nitrogen-containing compound of the formula (1) as the extraction solvent, so that cyclohexane is distilled from the top of the distillation column, and a mixed liquid of cyclohexene and the nitrogen-containing compound of the formula (1), is withdrawn from the bottom of the column, and the mixed liquid is subjected to distillation to separate cyclohexene.

5. The method for separating cyclohexene according to claim 1, wherein a mixture of cyclohexene and benzene is subjected to extractive distillation by means of the nitrogen-containing compound of the formula (1) as the extraction solvent, so that cyclohexene is distilled from the top of the distillation column, and a mixed liquid of benzene and the nitrogen-containing compound of the formula (1), is withdrawn from the bottom of the column.

6. The method for separating cyclohexene according to claim 1, wherein a mixture of cyclohexene, cyclohexane and benzene, is subjected to first extractive distillation by means of the nitrogen-containing compound of the formula (1) as the extraction solvent, so that a mixed liquid of benzene and the nitrogen-containing compound of the formula (1), is withdrawn from the bottom of the distillation column, and a mixed liquid of cyclohexene and cyclohexane, is distilled from the top of the column, thereby producing a distillate which is subjected to second extractive distillation by means of the nitrogen-containing compound of the formula (1) as the extraction solvent, so that cyclohexane is distilled from the top of the column, and a mixed liquid of cyclohexene and the nitrogen-containing compound of the formula (1), is withdrawn from the bottom of the column, and the mixed liquid is subjected to distillation to separate cyclohexene.

7. The method for separating cyclohexene according to claim 1, wherein a mixture of cyclohexene, cyclohexane and benzene is subjected to extractive distillation by means of the nitrogen-containing compound of the formula (1) as the extraction solvent, so that cyclohexane is distilled from the top of the distillation column, and a mixed liquid of cyclohexene, benzene and the nitrogen-containing compound of the formula (1), is withdrawn from the bottom of the column, and the mixed liquid is subjected to distillation, so that cyclohexene is distilled from the top of the column, and benzene and the nitrogen-containing compound of the formula (1), are withdrawn from the bottom of the column.

* * * * *

UNITED STATES PATENT AND TRADEMARK OFFICE
CERTIFICATE OF CORRECTION

PATENT NO. : 5,865,958
DATED : February 2, 1999
INVENTOR(S) : Yu Kanda, et al.

It is certified that error appears in the above-identified patent and that said Letters Patent is hereby corrected as shown below:

Column 10, Line 31, "formula (1), or a is" should read --formula (1), is--.

Signed and Sealed this

Twenty-first Day of September, 1999

Attest:

Q. TODD DICKINSON

*Attesting Officer*          *Acting Commissioner of Patents and Trademarks*